United States Patent [19]
Bonnefous

[11] Patent Number: 6,113,543
[45] Date of Patent: Sep. 5, 2000

[54] METHOD AND DEVICE FOR DETERMINING THE COMPLIANCE AND THE BLOOD PRESSURE OF AN ARTERY BY ULTRASONIC ECHOGRAPHY

[75] Inventor: Odile Bonnefous, Nogent sur Marne, France

[73] Assignee: U.S. Philips Corporation, New York, N.Y.

[21] Appl. No.: 09/077,414
[22] PCT Filed: Sep. 27, 1997
[86] PCT No.: PCT/IB97/01180
§ 371 Date: Sep. 2, 1998
§ 102(e) Date: Sep. 9, 1998
[87] PCT Pub. No.: WO98/14119
PCT Pub. Date: Apr. 9, 1998

[30] Foreign Application Priority Data

Sep. 30, 1996 [EP] European Pat. Off. .............. 96402081

[51] Int. Cl.[7] .................................. A61B 8/00; A61B 8/06
[52] U.S. Cl. ........................................... 600/438; 600/454
[58] Field of Search ........................... 600/438, 453–456, 600/485, 500, 504

[56] References Cited

U.S. PATENT DOCUMENTS

| | | | |
|---|---|---|---|
| 5,054,493 | 10/1991 | Cohn et al. | 600/485 |
| 5,107,840 | 4/1992 | Bonnefous | 600/454 |
| 5,316,004 | 5/1994 | Chesney et al. | 600/485 |
| 5,411,028 | 5/1995 | Bonnefous | 128/661.08 |
| 5,830,131 | 11/1998 | Caro et al. | 600/300 |

*Primary Examiner*—Francis J. Jaworski
*Attorney, Agent, or Firm*—Dwight H. Renfrew

[57] ABSTRACT

The invention relates to an ultrasonic echograph apparatus and method for locally determining biological data constituted by the time varying part of the blood pressure and the arterial wall compliance variations in function of the arterial radius variations, and includes the steps of measuring blood flow rate, arterial radius variation, and the mean arterial radius variation for two neighboring excitation lines and a hydrodynamic inductance. The method further includes steps of modelling, based on the measures, arterial wall behaviors by arterial wall stress-strain laws according to parametric relationships giving the biological data to determine, in the case of purely elastic or visco-elastic arterial behavior the parameters of the parametric relationships being related to the arterial dilatation and contraction phases over a whole cardiac cycle.

16 Claims, 4 Drawing Sheets

METHOD AND DEVICE FOR DETERMINING THE COMPLIANCE AND THE BLOOD PRESSURE OF AN ARTERY BY ULTRASONIC ECHOGRAPHY

BACKGROUND OF THE INVENTION

1. Field of the Invention

The present invention relates to a method for determining, by means of an ultrasonic echograph, the compliance and the blood pressure of an artery containing flowing blood, according to an artery model.

The invention also relates to an ultrasonic echograph having a system for carrying out said method.

2. Description of Related Art

Such a method is already known from the publication entitled "The Static Elastic Properties of 45 Human Thoracic and 20 Abdominal Aortas in Vitro and the Parameters of the Model" by G. J. LANGEWOUTERS et alii, published in "J. Biotech.,17, 1984, pp. 425–435". Said document discloses an artery model based on the hypothesis of pure elastic behaviour of arterial walls. First, direct measurements are obtained from IN VITRO experimentations, in static pressure conditions, and a pressure/arterial diameter diagramm is constructed from the experimental measurements. Then, a relationship (3) between the arterial cross-section and the pressure is established. Said relationship (3) called model is calculated based on Young's modulus (3a) which increases with pressure according to a second order function. Algebraic manipulation then integration of said modulus, taking into account boundary conditions, yields said general formulation (3) of the arterial cross-section (A(p)) value as a parametrical function of pressure (p), which only takes into account pure elastic behaviour of the artery. The derivative of said general formulation (3) with respect to pressure provides a formulation (4) of the static compliance (C(p)) as a parametrical function of pressure (p.428, col.1,2). The direct measurements and the results obtained by calculations using the model of a purely elastic artery are compared.

According to the author of this publication (p.429, col.1), these formulations (3,4) are valid for homogeneous, isotropic, piece-wise linear, purely elastic material with cylindrical cross-section. Thus, application to aortas is a gross approximation.

Nowdays, diagnosis of vascular diseases and therapeutic choices have to be based on the analysis of the arterial lesion morphology and on the analysis of blood flows. These informations must be obtained with accuracy, and without using invasive means.

SUMMARY OF THE INVENTION

The present invention aims at providing a method for determining the pressure and the compliance values of arterial walls, according to models now taking into account a more complex structure of said wails than that considered in the cited publication.

The aim of the invention is reached by a method according to claim 1.

Said method is much more efficient than a method based on this previous model.

Such an improvement of the new viscoelastic model is based on a better characterization of the mechanical behaviour of arterial walls, which results in that compliance and pressure are further more accurately defined and formulated.

An other object of the invention is to propose an ultrasonic echograph having a system to carry out said method.

This aim is achieved by an ultrasonic echograph according to claim 9.

This tool permits determining accurately and without using invasive means whether the examined artery fulfil efficiently its function of pressure wave guide, conveying the kinetic power generated by the cardiac pump while adapting the wave form to the downstream arterial system.

BRIEF DESCRIPTION OF THE DRAWINGS

The invention will now be described in further details with reference to the accompanying drawings, in which.

DESCRIPTION OF THE PREFERRED EMBODIMENTS

Figure 1:
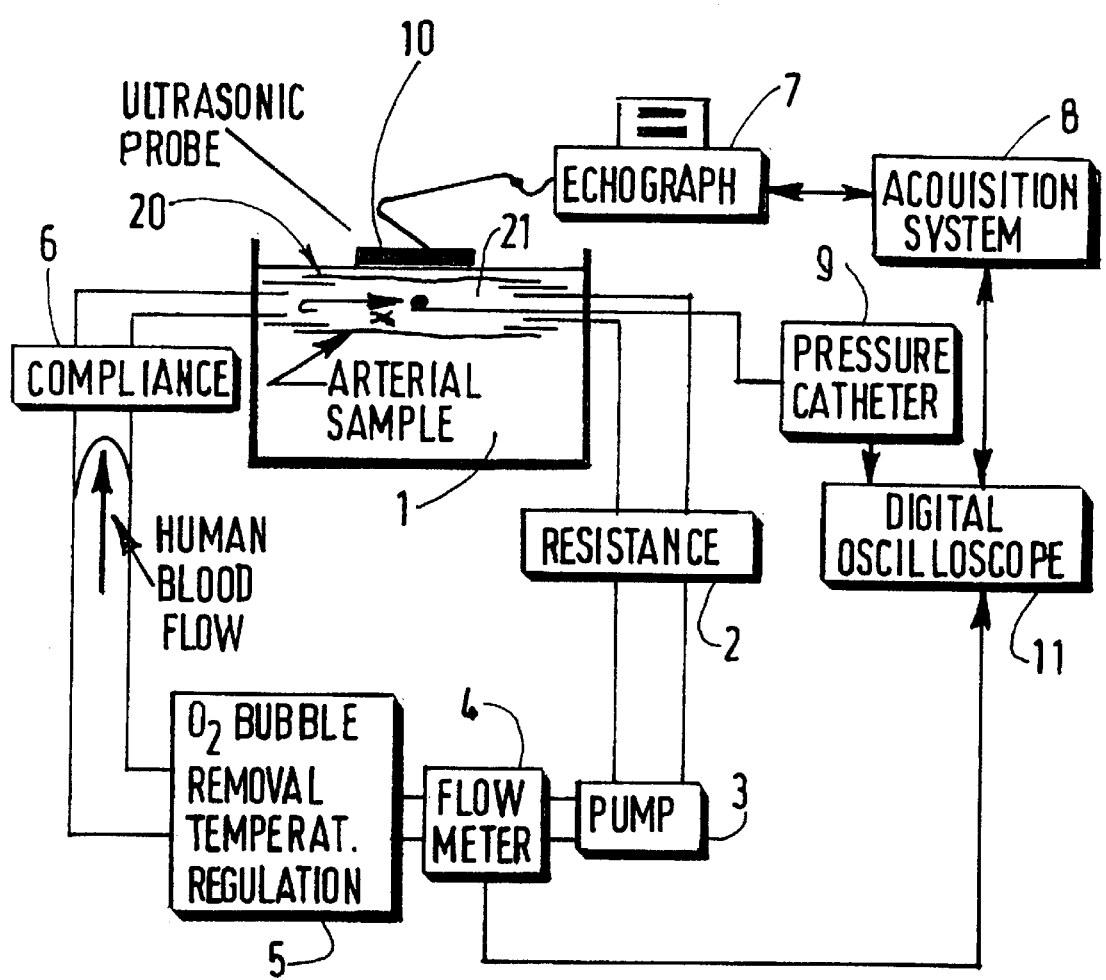
FIG. 1 shows diagrammatically a set-up for carrying out direct measurements of pressure and compliance of an arterial sample.

An echographic method for determining both the compliance and the pressure with respect to the radius of an artery containing flowing blood is described hereafter. This method comprises steps of measuring, by means of an ultrasonic echograph, standard echographic data which are easily acquired by non invasive means, and steps of processing said data according to a new artery model.

The steps of processing the acquired echographic data are dependent on a previous construction of a new stress-strain arterial wall model taking into account the complex mechanical behaviour of said artery with respect to blood flow. The construction of said new stress-strain arterial walls model is first described.

First of all, blood flow velocities and pressure in a purely elastic tube may be expressed from Bernouilli formulation known of those skilled in the art by linking pressure gradient and blood flow parameters according to the following formulation:

$$-\frac{dP}{dx} = RQ + L\frac{\partial Q}{\partial t} \quad (1a)$$

where P is the pressure, dP/dx is the pressure gradient along the longitudinal axis, called x axis, of the tube, and Q is the blood flow generated by said pressure gradient. The blood viscosity creates a constant hydrodynamic resistance R to the flow. The blood inertia is responsible for the $L\partial Q/\partial t$ term. L is a hydrodynamic inductance equal to $\rho/\pi r_0^2$ where $r_0$ is the mean arterial radius, and $\rho$ is the density of blood.

During a cardiac cycle there occur variations of the artery size with time allowing a local blood storage followed by a restitution of blood volume. The storage takes place during systole coresponding to the cardiac blood ejection, while the volume flow is restituted during diastole corresponding to the absence of cardiac blood outflow. This regulation of flow describes the basic arterial function. It closely depends on the arterial ability to be dilated with the pressure wave propagation. The distensibility, or compliance C, is defined by the following formulation:

$$C = \frac{\partial S}{\partial P} = 2\pi r_0 \frac{\partial r}{\partial P} \qquad (2)$$

where S is the area of the artery cross-section, r is the radius of the artery. When expressing the flow parameters in the above formulation (1a) as a function of the compliance C (2) instead of as a function of the pressure gradient, the formulation (1a) may be replaced by the following new general law:

$$-\frac{1}{C}\frac{\partial S}{\partial x} = RQ + L\frac{\partial Q}{\partial t} \qquad (1b)$$

linking flow Q and cross-section S independently of the pressure P, and implying intrinsic mechanical variables R and L of blood and the compliance C of arterial walls.

The arterial compliance C is a non linear function of the pressure P. This non linearity gives its genuine flow regulation ability to the artery. The method according to the present invention aims at determining the arterial compliance C from the general law (1b). However it is to be noted that a calculation of said compliance C by purely carrying out an inversion of general law (1b) would be tremendously complicated since it would be necessary to introduce this non linarity in the left term.

In the following description, two different behaviours of the artery will be considered for calculating the arterial compliance, i.e. a viscoelastic model and, for comparison, an elastic model of arterial walls. Until now, only elastic models had been considered in the state of the art, and are approximations substantially far from the actual behaviour of the arterial walls. For example, the purely elastic model of arterial walls which is disclosed in the Langewouters publication was further tested by IN VIVO and IN VITRO experiments. The Langewouters law (3) does not to determine the intrinsic parameters R and L and the compliance value C with a satisfactory confidence level. These results question the initial pure elastic hypothesis and leads eventually to the introduction of a viscous component in the parietal behaviour.

The general law (1b) which is used thereafter permits to take the viscoelastic behaviour of arteries into account. By algebraically manipulating said general law (1b), formulations of the variable part P(r) of the arterial pressure P with respect to the arterial radius r, and of the compliance C(r) also with respect to the arterial radius r are further calculated according to formulations (4a),(2b):

$$P(r) = K[\tan(\alpha + \beta(r - r_0)) - \tan \alpha], \qquad (4a)$$

$$C(r) = 2\pi r_0 \cos^2(\alpha + \beta(r - r_0))/(K\beta) \qquad (5a)$$

where K, $\alpha$, $\beta$, are the new model parameters and $r_0$ is the mean arterial radius. An identification method is further used consisting in tuning the parameters K, $\alpha$, $\beta$, in order to verify at best the general law (1b), by minimizing the resulting quadratic error related to thr equalization of the right and left terms of said general law (1b).

Figure 3:
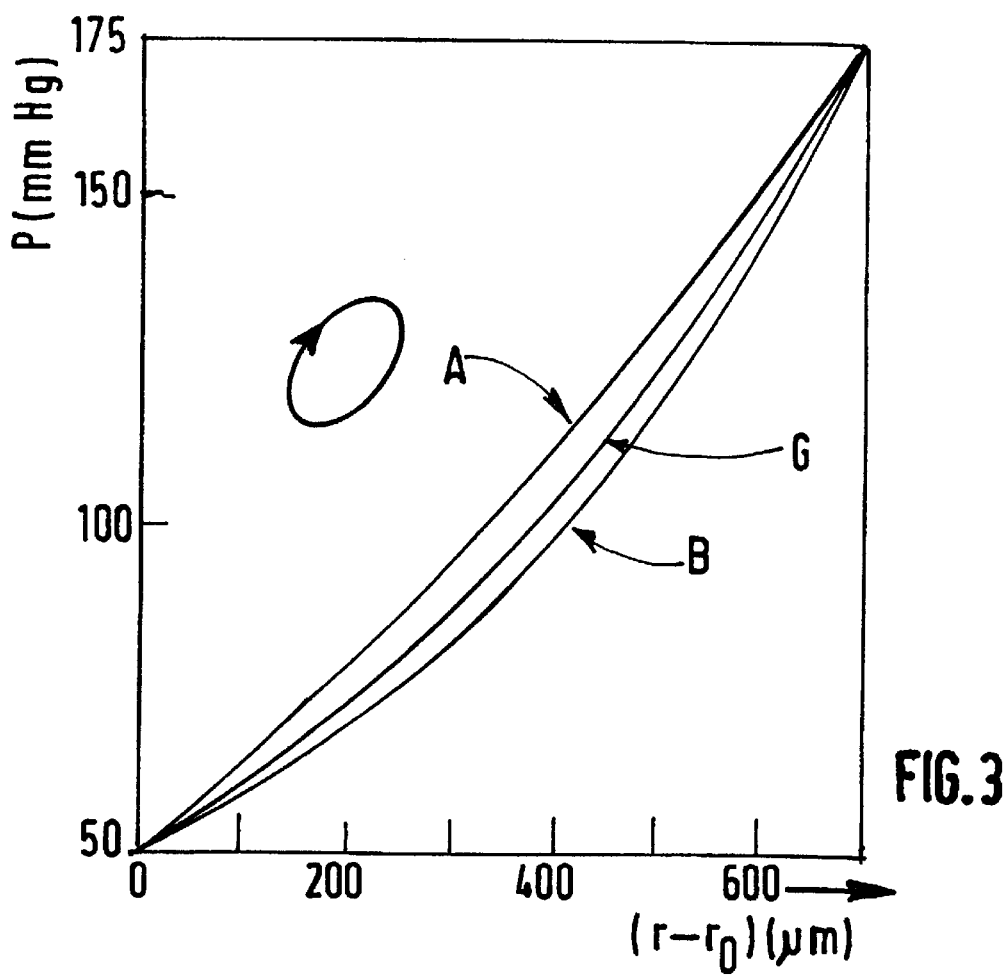
FIG. 3 shows pressure curves as functions of dilation with hysteresis A,B and without hysteresis G respectively corresponding to viscoelastic and to purely elastic arterial behaviours.

The viscoelastic behaviour of arteries is due to their complex structure. The compliance is dependent on the local arterial pressure at each instant and is different from the elasticity which is a constant of the materials. In the case of a viscoelastic medium, the stress due to the pressure P depends on both strain represented by the radius r and strain speed given by the partial derivative $\partial r/\partial t$. For example, FIG. 3 shows a graphic representation of P(r). The curve of the pressure P as a function of the arterial radius r presents an upper part noted A related to a systole, and a lower part noted B related to a diastole. So P(r) presents an hysteresis phenomenon which is characteristic of an arterial viscous behaviour. For modeling this hysteresis, it is chosen to parametrize separately the two phases, systole and diastole, of the cardiac cycle, while keeping the general law (1b). Thus, two sets of parameters $\alpha_d, \alpha_c$; $\beta_d, \beta_c$ corresponding respectively to the arterial dilation (d) or systole, and to the arterial contraction (c) or diastole during the return to the initial state, allow to completely describe the viscoelastic behaviour of the arterial wall. FIG. 3 also shows a curve G situated between curves A and B which corresponds to a purely elastic behaviour without hysteresis. In the case of purely elastic behaviour, dilation and contraction of the artery are performed according to the same law, then the two phases are modelized with only one set of parameters $K_s$, $\alpha_s$, $\beta_s$. It has been found that the actual behaviour of an artery rather leads to curves A, B.

The validation of the viscoelastic behaviour described above requires use of experimental data, by simultaneous measurements of arterial dilation and arterial pressure. For this purpose, IN VITRO direct measurements of the pressure and compliance have been carried out using an arterial set-up reproducing closely physiological conditions. Also, IN VIVO tests have been made for the experimental validation of these models.

Referring to FIG. 1, an arterial set-up is represented diagrammatically having means for performing IN VITRO direct measurements in physiological conditions as close as possible from living conditions. FIG. 1 shows an arterial sample 20 freshly taken from a cadaver and placed in a temperature regulated conservation bath 1. The sample 20 is perfused with total human blood 21 supplied by a blood transfusion center. The hematocrit is controlled during the experiment to verify the hemolysis degree and the blood viscosity. Heparin is used to prevent any coagulation of the system. The hemodynamic set-up is made up of an extracorporal peristaltic pump 3 interfaced with a frequency generator allowing pulsed flow generation, and of a dedicated conduction equipment ensuring a low hemolysis. A compliance 6 and a resistance 2 allow to adjust the flow and pressure data. A heat exchanger and an extracorporal circulation module 5 are placed in parallel to ensure a constant temperature, to oxygenate and eliminate bubbles.

Instrumentation allows on the one hand to control flow conditions, using an external flow-meter 4 and manometer, and on the other hand to acquire data. A pressure catheter 9 provides the intra luminal pressure, and an echograph 10 allows the recording of acoustic signals. The pressure data acquisition is performed using a digital oscilloscope 11, the ultrasound signals are stored in a dedicated acquisition system 8, and these two recording means are synchronized to avoid an artificial delay which would hide any viscous behaviour. The arterial diameter variations are derived by applying ultrasound signal processing techniques previously described in a U.S. Pat. No. 5,411,028 (EP 0 603 967) which is here incorporated by reference.

The use of the measurements of a purely elastic model and of a viscoelastic model are performed by minimizing the quadratic error between the measured pressure and the modelled one, for both models. The coefficient set K, α, β are adapted to realize this minimization. Using data extracted from seven common carotid arteries, the elastic model and the viscoelastic model are assessed through the residual quadratic error.

Figure 2A:
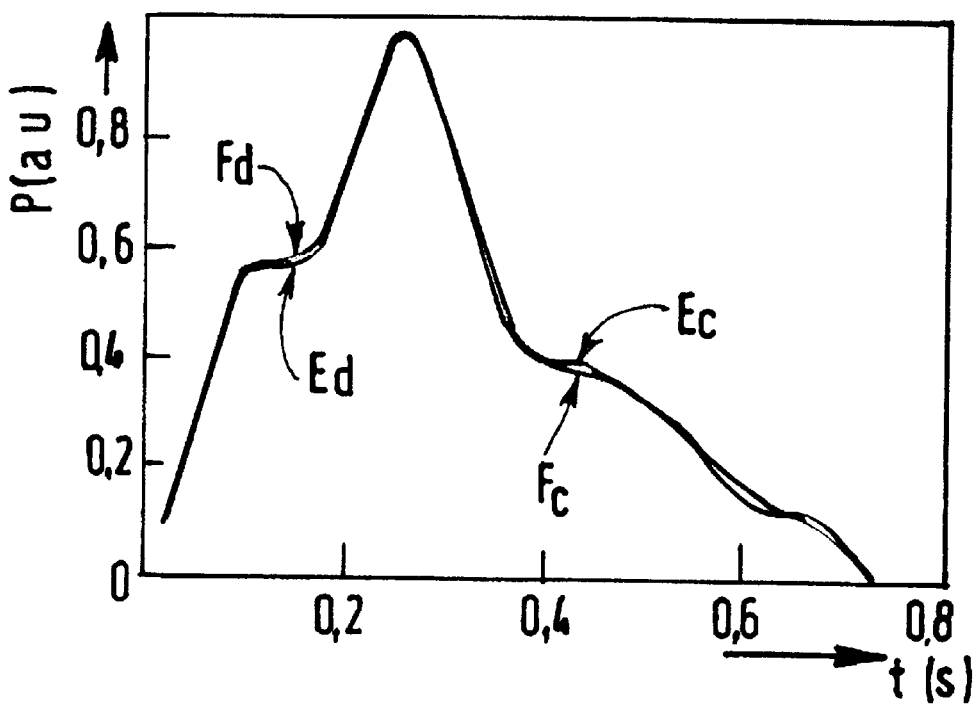
FIG. 2A shows a measured pressure curve E and a calculated pressure curve F obtained from the viscoelastic model now proposed.

FIG. 2A illustrates the viscoelastic model validity, by showing the measured pressure P and the pressure calculated by means of the viscoelastic model, as functions of time t, respectively on curves E and F. Said curves E and F are very close.

Figure 2B:
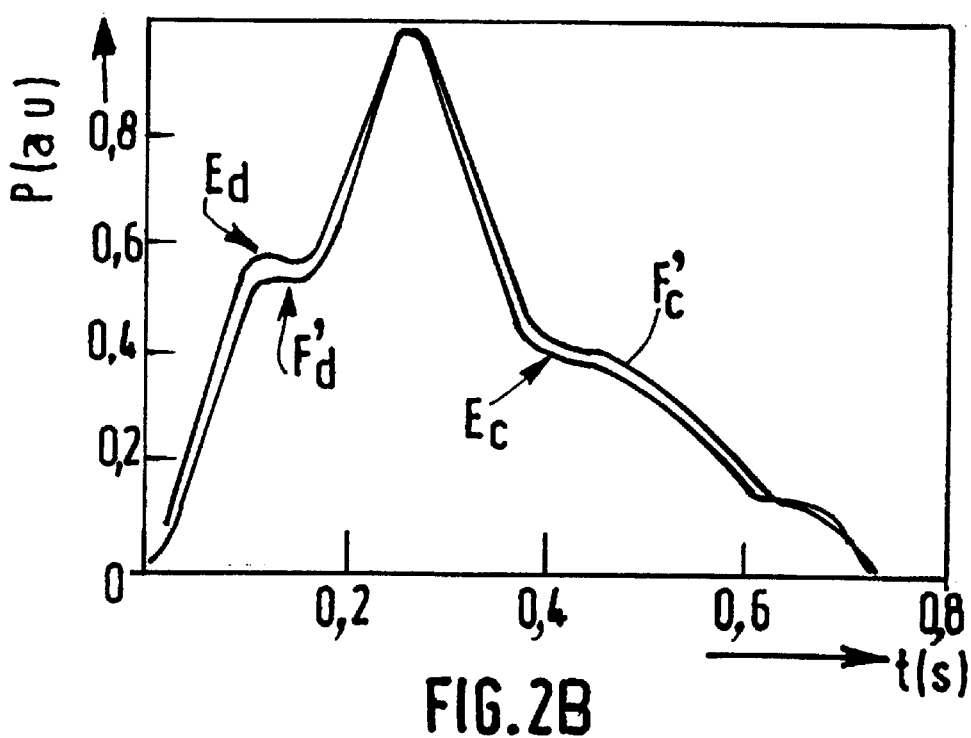
FIG. 2B shows a measured pressure curve E and a calculated pressure curve F' obtained from a purely elastic model.

FIG. 2B illustrates the elastic model validity, by showing the measured pressure P and the pressure calculated by means of the elastic model, as functions of time t, respectively on curves E and F'. Said curves E and F' are far from being superposed showing that the elastic model is not so valuable as the viscoelastic one. The curves have index d where the dilation phase is concerned, and index c when the contraction phase is concerned.

Figure 2C:
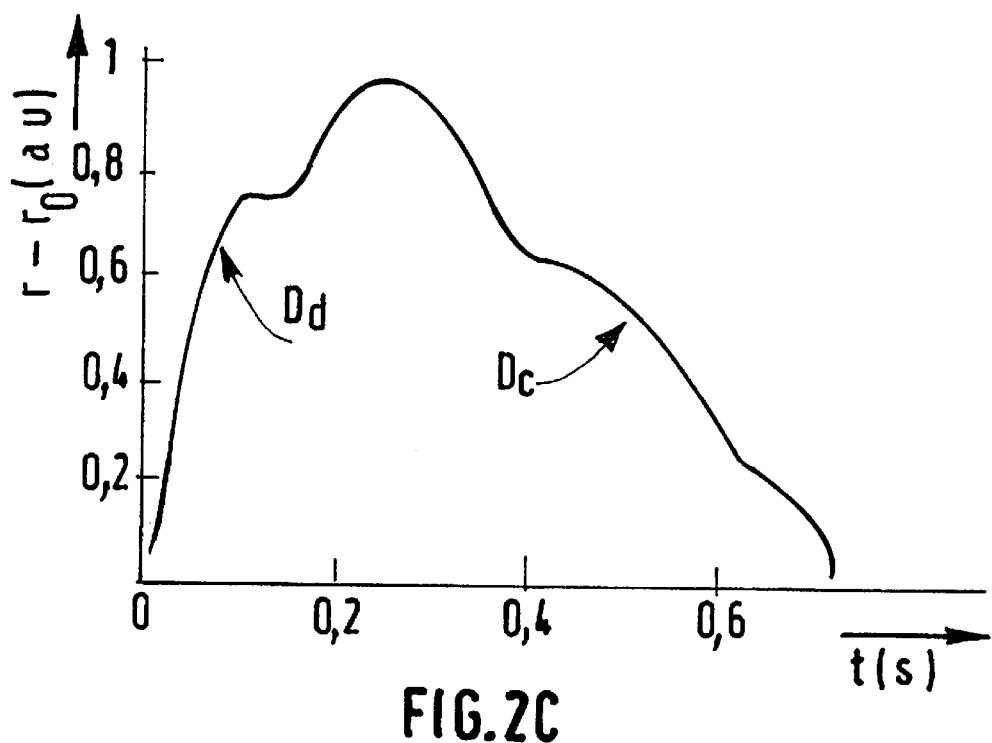
FIG. 2C shows a dilation curve D as a function of time.

FIG. 2C illustrates the measured dilation $r-r_0$ as a function of time t on curve D.

The models respectively show with respect to direct measurements in all the cases an error which is above 10% for the purely elastic model and below 1% for the viscoelastic one.

From a more precise mathematical point of view, the general law (1b) linking the pressure gradient dP/dx and blood flow parameters can also be expressed by (1c):

$$\frac{dP}{dx} = \left(\frac{\partial P}{\partial x}\right)_{r_0} + \frac{\partial P}{\partial r} \cdot \frac{\partial r}{\partial x} \quad (1c)$$

where x is the longitudinal axis of the artery. The first term $(\partial P/\partial x)_{r_0}$ is here considered related to the constant mean value ro of the arterial radius and is therefore a constant term responsible for the continuous component $RQ_0$ of the flow where $Q_0$ is the mean value of the flow Q according to (8b):

$$RQ_0 = \left(\frac{\partial P}{\partial x}\right)_{r_0} \quad (8b)$$

The time varying term of the pressure gradient is then (8d):

$$\frac{dp(t)}{dx} = \frac{\partial P}{\partial r} \cdot \frac{\partial r}{\partial x} \quad (1d)$$

and is related to the compliance C of relation (2a) which is tranformed into an equivalent relation:

$$C = 2\pi r_0 \gamma \quad (2c)$$

by setting $$\gamma = \frac{\partial r}{\partial p} \quad (26a)$$

for simplicity. The term $$\frac{\partial P}{\partial r}$$

is known as the variation in blood pressure with arterial wall radius, and the term $$\frac{\partial r}{\partial x}$$

is known as the arterial wall radius gradient.

The general law (1b) can be rewritten according to a new formulation (1c) providing a new general law (1e), as follows:

$$-\frac{dp(t)}{dx} = Rq + L\frac{dq}{dt} = -\frac{1}{\gamma}\frac{\partial r}{\partial x} \quad (1e)$$

with $$q = Q - Q_0 \quad (24)$$

The final transformation of the general law (1e) consists in introducing a stress-strain law in the expression Z (25):

$$\frac{dp(t)}{dx} = Z = \frac{1}{\gamma} \cdot \frac{\partial r}{\partial x} \quad (25)$$

A resolution using the mean square method then consists in calculating the minimal value of the quadratic error related to the left and right terms of the said general law (1e), according to a general formulation (11a) of said quadratic error:

$$E^2 = \left\| Rq + L\frac{dq}{dt} + \frac{1}{\gamma}\frac{dr}{dx} \right\|^2 \quad (11a)$$

The constants R and L are first easily extracted from equations $\partial E^2/\partial R=0$ and $\partial E^2/\partial L=0$ calculated by deriving the equation (11a), and are given thereafter by (9a) and (10a):

$$R = \frac{\langle q\frac{dq}{dt}\rangle\langle Z\frac{dq}{dt}\rangle - \langle\left(\frac{dq}{dt}\right)^2\rangle\langle q \cdot Z\rangle}{\langle\left(\frac{dq}{dt}\right)^2\rangle\langle q^2\rangle - \langle q\frac{dq}{dt}\rangle^2} \quad (9a)$$

$$L = \frac{\langle q \cdot \frac{dq}{dt}\rangle\langle Z \cdot q\rangle - \langle q^2\rangle\langle Z \cdot \frac{dq}{dt}\rangle}{\langle\left(\frac{dq}{dt}\right)^2\rangle\langle q^2\rangle - \langle q \cdot \frac{dq}{dt}\rangle^2} \quad (10a)$$

The resulting quadratic error becomes (11b):

$$E^2 = R^2\langle q^2\rangle + L^2\langle\frac{dq^2}{dt}\rangle + \langle Z^2\rangle + \\ 2RL \cdot \langle q \cdot \frac{dq}{dt}\rangle + 2R \cdot \langle Z\rangle + 2L \cdot \langle Z\frac{dq}{dt}\rangle \quad (11b)$$

where $\langle . \rangle$ = mean value of the concerned function over a cardiac cycle.

The parameters K, α, β inducing a minimum value of said quadratic error are considered as the solution of the problem. For this purpose, the time varying pressure gradient Z=dp (t)/dx (25) is then modeled according to the two different hypotheses:
either the artery is purely elastic,
or it is viscoelastic.

PURELY ELASTIC MODEL

It can be noted that according to FIG. 3, a purely cyclic phenomenon is involved only along curve G in two directions, corresponding to the cardiac cycle. In the case of such a cyclic phenomenon, when the summation involved by the integration is done during this cycle, the term:

$$\left\langle q \cdot \frac{dq}{dt} \right\rangle = 0$$

which simplifies the previous expressions (9a),(10a) to give R (9b) and L (10b):

$$R = -\frac{\left\langle q \cdot \frac{dq}{dx} \right\rangle}{\langle q^2 \rangle} \tag{9b}$$

$$L = -\frac{\left\langle Z \cdot \frac{dq}{dt} \right\rangle}{\left\langle \frac{dq^2}{dt} \right\rangle} \tag{10b}$$

and the quadratic error becomes:

$$E^2_{\alpha,\beta} = \langle Z^2 \rangle - \frac{\langle qZ \rangle^2}{\langle q^2 \rangle} - \frac{\left\langle Z \frac{dq}{dt} \right\rangle}{\left\langle \frac{dq^2}{dt} \right\rangle} \tag{11c}$$

and the associated normalized quadratic error is:

$$E^2_{norm(\alpha,\beta)} = \frac{E^2_{\alpha,\beta}}{\langle Z^2 \rangle} \tag{11d}$$

which is independant of the parameter K.
Considering the following general model (4b) and the general law (1e):

$$P_{\alpha,\beta,K} = K \cdot [\tan(\alpha + \beta(r - r_0)) - \tan\alpha] \tag{4b}$$

$$\left(\frac{dp(t)}{dx}\right)_{\alpha,\beta,K} = \frac{\partial P}{\partial r} \cdot \frac{\partial r}{\partial x} = \frac{1}{K\beta \cdot \cos^2(\alpha + \beta(r - r_0))} \cdot \frac{\partial r}{\partial x} \tag{1f}$$

where $$\gamma = K\beta \, \text{Cos}^2(\alpha + \beta(r - r_0)) \tag{26b}$$

is a parametric relationship introducing the stress-strain law in the term Z.

With the first hypothesis of a purely elastic model, α and β are considered as constants during the cardiac cycle: dilation and contraction of the artery are performed with the same stress-strain law, as shown on FIG. 3, according to curve G. The normalized quadratic error is then:

$$E^2_{norm(\alpha,\beta)} = 1 - \frac{\langle q \cdot Z \rangle^2}{\langle q^2 \rangle \langle Z^2 \rangle} - \frac{\left(\frac{dq}{dt} \cdot Z\right)^2}{\left\langle \frac{dq}{dt} \right\rangle^2 \langle Z^2 \rangle} \tag{11e}$$

where the formula (26b) is used to compute Z (25).
The best solution is found for specific values ($\alpha_S$, $\beta_S$) minimizing the normalized quadratic error (11e).
Now $\alpha_S$ and $\beta_S$ may be determined, and $K_S$ is computed thanks to the expression (10b) where L is already known by:

$$K_S = -\frac{1}{L} \cdot \frac{\left\langle \frac{1}{\beta_S \cdot \cos^2(\alpha_S + \beta_S(r - r_0))} \cdot \frac{\partial r}{\partial x} \cdot \frac{dq}{dt} \right\rangle}{\left\langle \frac{dq^2}{dt} \right\rangle} \tag{15}$$

Finally: $P(r) = K_S \cdot [\tan(\alpha_S + \beta_S(r - r_0)) - \tan(\alpha_S)]$ (4c)

$$C(r) = 2\pi r_0 \cdot \frac{\partial r}{\partial P} = 2\pi r_0 \cos^2(\alpha_S + \beta_S(r - r_0))/(K\beta_S) \tag{2c}$$

VISCOELASTIC MODEL

With the second hypothesis of a viscoelastic model, the dilation and contraction phases of the artery correspond to the same kind of model but with different (α, β) solutions. That allows to introduce the hysteresis phenomenon in the stress-strain laws. However the resolution becomes more sophisticated since the term <q.dq/dt> cannot be set to 0, the integration being made on each part of the cardiac cycle separately. For each part of the cardiac cycle, the following computation is then required:

(a) R and L, with the formulas (9a) and (10a);
(b)

$$E^2_{norm(\alpha,\beta)} = E^2_{(\alpha,\beta)}/\langle Z^2 \rangle \tag{11d},$$

which is independent of K, this last computation of $E^2_{norm(\alpha,\beta)}$ (11d) being derived from the expression (11c) by a division of all terms by $\langle Z^2 \rangle$, with two parameters ($\alpha_d$, $\beta_d$) for the dilation and with two parameters ($\alpha_c$, $\beta_c$) for the contraction, determined by minimizing $E^2_{norm(\alpha,\beta)}$ (11d);

(c) a continuity condition is also necessary when the pressure P and the arterial radius $r_{max}$ are maximum:

$$P(r_{max}) = K_d \cdot [\tan(\alpha_d + \beta_d(r_{max} - r_0)) - \tan(\alpha_d)] \tag{17a}$$

$$= K_c \cdot [\tan(\alpha_c + \beta_c(r_{max} - r_0)) - \tan(\alpha_c)] \tag{17b}$$

The final solution is therefore given by P(r) whose components are $P_d(r)$ which is the pressure variation during dilation and $P_c(r)$ which is the pressure variation during contraction:

$$P_d(r) = K \times a[\tan(\alpha_d + \beta_d(r - r_0)) - \tan(\alpha_d)] \tag{4d}$$

$$P_c(r) = K[\tan(\alpha_c + \beta_c(r - r_0)) - \tan(\alpha_c)] \tag{4e}$$

$$\text{with: } a = \frac{K_d}{K_c} = \frac{\tan(\alpha_c + \beta_c(r_{max-r_0})) - \tan(\alpha_c)}{\tan(\alpha_d + \beta_d(r_{max-r_0})) - \tan(\alpha_d)} \tag{18}$$

and with:

$$K = -T_d - T_c \tag{19}$$

$T_d$, $T_c$ being given by:

$$T_d = \frac{1}{L} \cdot \frac{\left\langle \frac{a}{\beta_d \cdot \cos^2(\alpha_d + \beta_d(r - r_0))} \cdot \frac{\partial r}{\partial x} \cdot \frac{dq}{dt} \right\rangle_{\text{(dil.)}}}{\left\langle \frac{dq^2}{dt} \right\rangle_{\text{(cycle)}}} \tag{20a}$$

-continued $$T_c = \frac{1}{L} \cdot \frac{\left\langle \frac{1}{\beta_c \cdot \cos^2(\alpha_c + \beta_c(r - r_0))} \cdot \frac{\partial r}{\partial x} \cdot \frac{dq}{dt} \right\rangle \text{(contr.)}}{\left\langle \frac{dq^2}{dt} \right\rangle \text{(cycle)}} \quad (20b)$$

where "dil." is for "dilation" and "contr." for "contraction". The final solution is also given by C(r) whose components are the compliance variation during dilation $C_d(r)$ and the compliance variation during contraction $C_c(r)$:

$$C_d(r) = 2\pi r_0 \cos^2(\alpha_d + \beta_d(r - r_o))/K\beta_d \cdot a \quad (2d)$$

$$C_c(r) = 2\pi r_o \cos^2(\alpha_c + \beta_c(r - r_o))/K\beta_c \quad (2e)$$

ECHOGRAPHIC METHOD FOR DETERMINING THE COMPLIANCE

By means of the use of such models according to the laws expressed by equations (4c) and (2c) for the purely elastic model, and by equations (4d,4e) and (2d,2e) for the viscoelastic model, an echographie method may be carried out using non invasive ultrasonic measurements including steps of measuring and determining the instantaneous blood flow rate Q(t) within the artery, the instantaneous radius variation r(t) of the artery, a mean radius ro of the artery along a first excitation line, and along a second excitation line, neighbouring the first excitation line, and the hydrodynamic inductance L.

This echographic method, which is disclosed by U.S. Pat. No. 5,411,028 (EP0603967) involves time domain correlation techniques applied to ultrasonic signals, which track the echoes with time and allow the estimation of the displacements of the corresponding biological structures. The flow function Q(t) is calculated by integration of the velocity profiles measured along the acoustic beam axis. The arterial radius r(t) are determined by locally measuring displacements of front arterial wall and posterior arterial wall and combining them to finally obtain an arterial dilation value r.

Thanks to the present method, it is now possible to introduce an appropriate arterial stress-strain law in this vascular procedure. Further steps are described hereafter for the non invasive and accurate extraction of the arterial pressure P(r) and compliance (Cr). This new method leads to a genuine breakthrough of vascular echography, allowing the early detection of cardio-vascular diseases and improving the therapeutic follow-up.

These steps may be carried out using computation means added to the already present computation means of the ultrasonic echograph described in the above cited US patent. These steps are different according to the two models: elastic or viscoelastic artery model.

Steps for Determining P(r) and C(r) According to the Purely Elastic Model

Initializing a set of predetermined parameters values $\alpha, \beta$ in a given range;

Calculating the derivative dq/dt and dr/dx from the measured values of Q(t), $Q_0$ and r(t), $r_0$;

Calculating a set of values of KZ from (25) corresponding to the set of values of $\alpha, \beta$;

Calculating R and L from (9b), (10b);

Calculating a set of values of the normalized quadratic error $E_{norm}$ from (11c), corresponding to the set of values of KZ;

Determining the minimal value of $E_{norm}$ among the values of $E_{norm}$ of this set;

Determining the corresponding values of the parameters $\alpha_S$, $\beta_S$ which provide said minimal value of $E_{norm}$;

Calculating the parameter value K from (15), and finally calculating P(r) from (4c)

C(r) from (2c)

Figure 4:
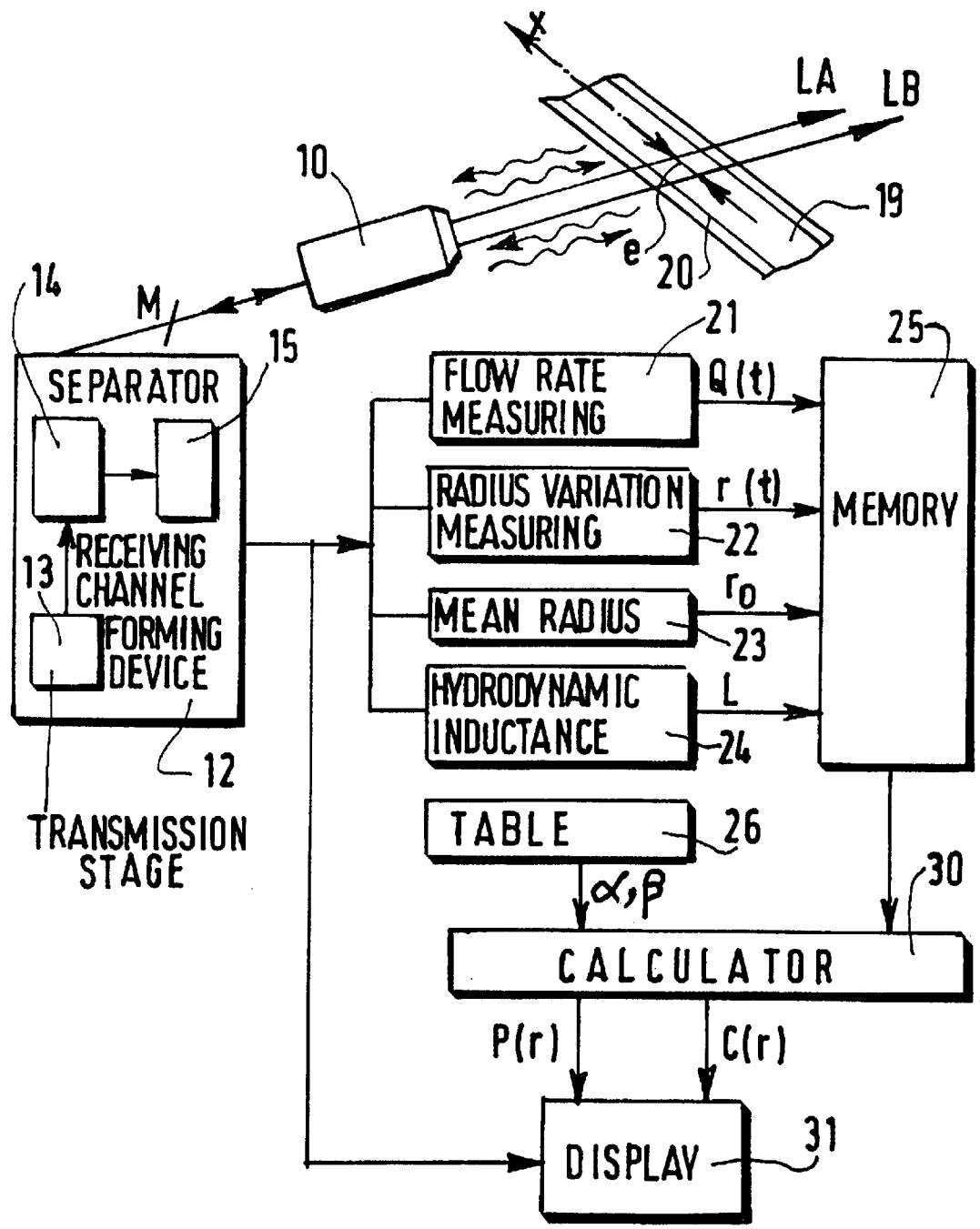
FIG. 4 shows diagrammatically an ultrasonic echograph having means for determining arterial pressure P(r) and compliance C(r) according to a model.

Occasionnaly displaying the curves P(r) and C(r) using display means 31 coupled to the computation output of the computation means 30 of the ultrasonic echograph as shown on FIG. 4.

Steps for Determining P(r) and C(r) According to the Viscoelastic Model.

Initializing a set of predetermined parameters $\alpha, \beta$ in a given range

Calculating the derivative dq/dt and dr/dt from the measured values of Q(t), $Q_0$, r(t) and $r_0$;

Calculating a set of values of KZ from (25) corresponding to the set of values of $\alpha, \beta$;

Calculating R and L from (9a) and (10a);

Calculating a set of values of the normalized quadratic error $E_{norm}$ from (11d), corresponding to the set of values of KZ (25);

Determining two minimal values of $E_{norm}$ among the values of $E_{norm}$ (11d) of this set;

Determining the corresponding values $\alpha_c$, $\alpha_d$ and $\alpha_d$, $\beta_d$ providing said two minimal quadratic errors;

Calculating the "a" parameter from 18 with 17a, 17b;

Calculating the "K" parameter from 19 with 20a, 20b, and finally calculating $P_d(r)$ (4d) with $\alpha_d$, $\beta_d$, a and K $P_c(r)$ (4d) with $\alpha_c$, $\beta_c$ and K $C_d(r)$ (2d) with $\alpha_d$, $\beta_d$, a, K and (r,$r_0$)

$C_c(r)$ (2e) with $\alpha_c, \beta_c$, K and (r,$r_0$).

The diagram of FIG. 4 represents an ultrasonic echograph for carrying out the method described above. This echograph permits of determining physiological data related to an artery 19,20 containing flowing blood. This device comprises a piezoelectric transducer 10 which may comprise a plurality of elementary transducers, and transmission/receiving means 12 which include at least a transmission stage 13, a separator 14 for separating the transmission stage 13 from the measuring units 21, 22, 23, 24, and a device 15 for forming receiving channels with the different signals received by the different elementary transducers. The elementary transducers are controled in order to selection any excitation line without displacement of the transducer 10. The lines, for example LA, LB are situated in the same plane, in a parallel configuration. The device 15 for forming channels supplies the downstream signal processing circuits 21, 22, 23, 24 with output signals.

The units 21, 22, 23, 24 provide respectively measures of the instantaneous blood flow rate Q(t), of the arterial radius r(t), of the arterial mean radius ro, and of the hydrodynamic inductance L, based on two output signals of the unit 12 corresponding to two excitation lines LA, LB separated by a distance e taken in the direction of the axis x of the artery 19,20. These data are stored in a memory 25 and provided to a calculator 30. A table 26 provides predetermined parameters $\alpha, \beta$. The calculator 30 calculates the time varying part of the blood pressure P(r) and the arterial wall compliance C(r) according to the calculation steps already described.

An ultrasonic image of the artery 19, 20, or indications of the values of P(r) or C(r) may be displayed on a screen 31 or provided to standard registration means.

All references cited herein, as well as the priority document European Patent Application 96402081.2 filed Sep. 30, 1996, are incorporated herein by reference in their entirety and for all purposes to the same extent as if each individual publication or patent or patent application was specifically and individually indicated to be incorporated by reference in its entirety for all purposes.

What is claimed is:

1. A method for determining biological data locally related to an artery containing flowing blood by means of an ultrasonic echograph, said echograph having non invasive means for providing measures of the blood flow rate, the instantaneous arterial radius variation, and the mean arterial radius for two neighbouring excitation lines traversing said artery, and for providing a measure of an hydrodynamic inductance value, said method comprising:

modeling on the basis of said provided measures the arterial wall behaviour by arterial wall stress-strain laws according to parametric relationships linking biological data including pressure and compliance variations to the radius variations of said artery either (i) during whole cardiac cycles, or (ii) during dilation phases of said cardiac cycles, or (iii) during contraction phases of said cardiac cycles, said parametric relationships having separate parameters related (i) to said whole cardiac cycles, (ii) to said dilation phases or (iii) to said contraction phases, respectively.

2. A method according to claim 1, further comprising:

computing the terms of a general law linking a blood pressure gradient to the blood flow rate and to blood flow rate time variations, and determining said parameters related to said whole cardiac cycles as the solutions of a least square method applied over a whole cardiac cycle to said computed terms.

3. A method according to claim 2, further comprising:

determining said parameters related to said whole cardiac cycles as constants over the whole cardiac cycle for modeling a purely elastic arterial wall behaviour by the same stress-strain law during dilation and contraction phases of a whole cardiac cycle.

4. A method according to claim 3, wherein said parameters related to said whole cardiac cycles further comprise values designated as $\alpha_s$, $\beta_s$, and $K_s$, and wherein said parameters related to said whole cardiac cycles model purely elastic arterial wall behaviour and provide, as a function of the arterial wall radius variations, designated as r, the pressure variations, designated as P(r), and the arterial wall compliance, designated as C(r), over a whole cardiac cycle further, and further comprising the step of:

determining said values $\alpha_s$, $\beta_s$, $K_s$ according to the following parametric relationships:

$$P(r) = K_s[\tan(\alpha_s + \beta_s(r - r_0)) - \tan(\alpha_s)]$$

$$C(r) = 2\pi r_0 \cdot \cos^2(\alpha_s + \beta_s(r - r_0))/(K\beta_s)$$

with $r_0$ being the mean arterial radius.

5. A method according to claim 2, further comprising:

determining said parameters related to said dilation phases and said parameters related to said contraction phases as non constant over the whole cardiac cycle for modeling a viscoelastic arterial wall behaviour by two different stress-strain laws, a first law during dilation phases and a second law during contraction phases, according to which laws the blood pressure variations as a function of the radius variations show an hysteresis phenomenon with continuity conditions for the highest pressure value or for the largest arterial radius.

6. A method according to claim 5 wherein said parameters related to said dilation phases further comprise values designated $\alpha_d$, $\beta_d$, K, wherein said parameters related to said contraction phases further comprise values designated as $\alpha_c$, $\beta_c$, K, and wherein said parameters related to said dilation phases and to said contraction phases model viscoelastic arterial wall behaviour and provide, as a function of the arterial wall radius variations, designated r, the pressure variations, designated $P_d(r)$ and $P_c(r)$, and the arterial wall compliance, designated $C_d(r)$ and $C_c(r)$, in the dilation and contraction phases, respectively, of a whole cardiac cycle and with continuity for the maximal pressure or radius, and further comprising the step of:

determining said values $\alpha_c$, $\beta_c$, $\alpha_d$, $\beta_d$, and K according to the following parametric relationships:

$$P_d(r) = K \times a[\tan(\alpha_d + \beta_d(r - r_0)) - \tan(\alpha_d)]$$

$$P_c(r) = K[\tan(\alpha_c + \beta_c(r - r_0)) - \tan(\alpha_c)]$$
$$C_d(r) = 2\pi r_0 \cos^2(\alpha_d + \beta_d(r - r_0))/K\beta_d \cdot a$$
$$C_c(r) = 2\pi r_0 \cos^2(\alpha_c + \beta_c(r - r_0))/K\beta_c$$

with $a = K_d/K_c = \dfrac{\tan(\alpha_c + \beta_c(r_{\max} - r_0)) - \tan(\alpha_c)}{\tan(\alpha_d + \beta_d(r_{\max} - r_0)) - \tan(\alpha_d)}$ and with $K = -T_d - T_c$ where $T_d$ and $T_c$ are given by $$T_d = \frac{1}{L} \cdot \frac{\left\langle \dfrac{a}{\beta_d \cdot \cos^2(\alpha_d + \beta_d(r - r_0))} \cdot \dfrac{\partial r}{\partial x} \cdot \dfrac{dq}{dt} \right\rangle (\text{dil.})}{\left\langle \dfrac{dq^2}{dt} \right\rangle (\text{cycle})}$$

$$T_c = \frac{1}{L} \cdot \frac{\left\langle \dfrac{1}{\beta_c \cdot \cos^2(\alpha_c + \beta_c(r - r_0))} \cdot \dfrac{\partial r}{\partial x} \cdot \dfrac{dq}{dt} \right\rangle (\text{contr.})}{\left\langle \dfrac{dq^2}{dt} \right\rangle (\text{cycle})},$$

and further with $r_0$ being the mean arterial radius.

7. A method according to claim 6, wherein the said separate parameters related to said whole cardiac cycles, to said dilation phases and to said contraction phases each comprise three individual parameters, and further comprising:

calculating blood flow rate variations and an arterial wall radius gradient between the two excitation lines from said provided measures, calculating the terms of the general law rewritten to include a further law linking the blood pressure gradient with the arterial wall radius gradient and the variations in blood pressure with arterial wall radius, and determining said separate parameters as solutions of a least square method using a normalized quadratic error applied to said calculated terms by initializing sets of two predetermined parameters related to said whole cardiac cycles, to said dilation phases and to said contraction phases, respectively, calculating the normalized quadratic error relative to said calculated terms expressed as a function of the sets of two predetermined parameters, calculating the minimal value of said normalized quadratic error, determining the set of two parameters for modeling an elastic arterial wall behaviour, or two sets of two parameters for modeling the viscoelastic arterial wall behaviour, which correspond to minimum values of the normalized quadratic error, and each of said separate sets of parameters from the determined sets of two parameters and an hydrodynamic inductance, and computing arterial pressure and arterial wall compliance from said sets of separate parameters according respectively to the elastic model or to the viscoelastic model.

8. A method according to claim 5, wherein the said separate parameters related to said whole cardiac cycles, to said dilation phases and to said contraction phases each comprise three individual parameters, and further comprising:

calculating blood flow rate variations and an arterial wall radius gradient between the two excitation lines from said provided measures, calculating the terms of the general law rewritten to include a further law linking the blood pressure gradient with the arterial wall radius gradient and the variations in blood pressure with arterial wall radius, and determining said separate parameters as solutions of a least square method using a normalized quadratic error applied to said calculated terms by initializing sets of two predetermined parameters related to said whole cardiac cycles, to said dilation phases and to said contraction phases, respectively, calculating the normalized quadratic error relative to said calculated terms expressed as a function of the sets of two predetermined parameters, calculating the minimal value of said normalized quadratic error, determining the set of two parameters for modeling an elastic arterial wall behaviour, or two sets of two parameters for modeling the viscoelastic arterial wall behaviour, which correspond to minimum values of the normalized quadratic error, and calculating the third parameter of each of said separate sets of parameters from the determined sets of two parameters and an hydrodynamic inductance, and computing arterial pressure and arterial wall compliance from said sets of separate parameters according respectively to the elastic model or to the viscoelastic model.

9. A method according to claim 2, further comprising:

deriving said parametric relationships giving the pressure and the compliance from said general law, determining a quadratic error between the terms of said general law, expressed as functions of said parameters of the parametric relationships related to said whole cardiac cycles, determining parameter values which minimize said quadratic error, and selecting said parameter values as said parameters of the parametric relationships related to said whole cardiac cycles.

10. A method according to claim 9, further comprising:

determining said parameters related to said whole cardiac cycles as constants over the whole cardiac cycle for modeling a purely elastic arterial wall behaviour by the same stress-strain law during dilation and contraction phases of a whole cardiac cycle.

11. A method according to claim 10, wherein said parameters related to said whole cardiac cycles further comprise values designated $\alpha_s$, $\beta_s$, and $K_s$, and wherein said parameters related to said whole cardiac cycles model purely elastic arterial wall behaviour and provide, as a function of the arterial wall radius variations, designated as r, the pressure variations, designated as P(r), and the arterial wall compliance, designated as C(r), over a whole cardiac cycle further, and further comprising the step of:

determining said values $\alpha_s$, $\beta_s$, $K_s$ according to the following parametric relationships:

$P(r) = K_s[\tan(\alpha_s + \beta_s(r-r_0)) - \tan(\alpha_s)]$ $C(r) = 2\pi r_0 \cdot \cos^2(\alpha_s + \beta_s(r-r_0))/(K\beta_s)$ with $r_0$ being the mean arterial radius.

12. A method according to claim 9, further comprising:

determining said parameters related to said dilation phases and said parameters related to said contraction phases as non constant over the whole cardiac cycle for modeling a viscoelastic arterial wall behaviour by two different stress-strain laws, a first law during dilation phases and a second law during contraction phases, according to which laws the blood pressure variations as a function of the radius variations show an hysteresis phenomenon with continuity conditions for the highest pressure value or for the largest arterial radius.

13. A method according to claim 12 wherein said parameters related to said dilation phases further comprise values designated as $\alpha_d$, $\beta_d$, K, wherein said parameters related to said contraction phases further comprise values designated as $\alpha_c$, $\beta_c$, K, and wherein said parameters related to said dilation phases and to said contraction phases model viscoelastic arterial wall behaviour and provide, as a function of the arterial wall radius variations, designated r, the pressure variations, designated $P_d(r)$ and $P_c(r)$, and the arterial wall compliance, designated $C_d(r)$ and $C_c(r)$, in the dilation and contraction phases, respectively, of a whole cardiac cycle and with continuity for the maximal pressure or radius, and further comprising the step of:

determining said values $\alpha_c$, $\beta_c$, $\alpha_d$, $\beta_d$, and K according to the following parametric relationships:

$$P_d(r) = K \times a[\tan(\alpha_d + \beta_d(r - r_0)) - \tan(\alpha_d)]$$

$$P_c(r) = K[\tan(\alpha_c + \beta_c(r - r_0)) - \tan(\alpha_c)]$$
$$C_d(r) = 2\pi r_0 \cos^2(\alpha_d + \beta_d(r - r_0))/K\beta_d \cdot a$$
$$C_c(r) = 2\pi r_0 \cos^2(\alpha_c + \beta_c(r - r_0))/K\beta_c$$

with $a = K_d/K_c = \dfrac{\tan(\alpha_c + \beta_c(r_{\max} - r_0)) - \tan(\alpha_c)}{\tan(\alpha_d + \beta_d(r_{\max} - r_0)) - \tan(\alpha_d)}$ and with $K = -T_d - T_c$ where $T_d$ and $T_c$ are given by $$T_d = \frac{1}{L} \cdot \frac{\left\langle \dfrac{a}{\beta_d \cdot \cos^2(\alpha_d + \beta_d(r - r_0))} \cdot \dfrac{\partial r}{\partial x} \cdot \dfrac{dq}{dt} \right\rangle \text{(dil.)}}{\left\langle \dfrac{dq^2}{dt} \right\rangle \text{(cycle)}}$$

$$T_c = \frac{1}{L} \cdot \frac{\left\langle \dfrac{1}{\beta_c \cdot \cos^2(\alpha_c + \beta_c(r - r_0))} \cdot \dfrac{\partial r}{\partial x} \cdot \dfrac{dq}{dt} \right\rangle \text{(contr.)}}{\left\langle \dfrac{dq^2}{dt} \right\rangle \text{(cycle)}},$$

and further with $r_0$ being the mean arterial radius.

14. A method according to claim 13, wherein the said separate parameters related to said whole cardiac cycles, to said dilation phases and to said contraction phases each comprise three individual parameters, and further comprising:

calculating blood flow rate variations and an arterial wall radius gradient between the two excitation lines from said provided measures, calculating the terms of the general law rewritten to include a further law linking the blood pressure gradient with the arterial wall radius gradient and the variations in blood pressure with arterial wall radius, and determining said separate parameters as solutions of a least square method using a normalized quadratic error applied to said calculated terms by initializing sets of two predetermined parameters related to said whole cardiac cycles, to said dilation phases and to said contraction phases, respectively, calculating the normalized quadratic error relative to said calculated terms expressed as a function of the sets of two predetermined parameters, calculating the minimal value of said normalized quadratic error, determining the set of two parameters for modeling an elastic arterial wall behaviour, or two sets of two parameters for modeling the viscoelastic arterial wall behaviour, which correspond to minimum values of the normalized quadratic error, and calculating the third parameter of each of said separate sets of parameters from the determined sets of two parameters and an hydrodynamic inductance, and computing arterial pressure and arterial wall compliance from said sets of separate parameters according respectively to the elastic model or to the viscoelastic model.

15. A method according to claim 12, wherein the said separate parameters related to said whole cardiac cycles, to said dilation phases and to said contraction phases each comprise three individual parameters, and further comprising:

calculating blood flow rate variations and an arterial wall radius gradient between the two excitation lines from said provided measures, calculating the terms of the general law rewritten to include a further law linking the blood pressure gradient with the arterial wall radius gradient and the variations in blood pressure with arterial wall radius, and determining said separate parameters as solutions of a least square method using a normalized quadratic error applied to said calculated terms by initializing sets of two predetermined parameters related to said whole cardiac cycles, to said dilation phases and to said contraction phases, respectively, calculating the normalized quadratic error relative to said calculated terms expressed as a function of the sets of two predetermined parameters, calculating the minimal value of said normalized quadratic error, determining the set of two parameters for modeling an elastic arterial wall behaviour, or two sets of two parameters for modeling the viscoelastic arterial wall behaviour, which correspond to minimum values of the normalized quadratic error, and calculating the third parameter of each of said separate sets of parameters from the determined sets of two parameters and an hydrodynamic inductance, and computing arterial pressure and arterial wall compliance from said sets of separate parameters according respectively to the elastic model or to the viscoelastic model.

16. An ultrasonic echograph for determining biological data locally related to an artery containing flowing blood comprising:

transmitting and receiving means, means for carrying out a method according to claim 1, further including:

a first sub-assembly for providing, for two excitation lines, measures of the blood flow rate, the arterial radius variations, and the mean arterial radius and also for providing an hydrodynamic inductance, a second sub-assembly for modeling, on the basis of said provided measures, the arterial wall behaviour by arterial wall stress-strain laws according to parametric relationships linking the biological data including the pressure and the compliance variations to the radius variations of said artery either (i) during whole cardiac cycles, or (ii) during dilation of said cardiac cycles or (iii) during contraction phases of said cardiac cycles, said parametric relationships having separate parameters related (i) to said whole cardiac cycles, (ii) to said dilation phases, or (iii) to said contraction phases, respectively, and a display system for displaying the ultrasonic images of the artery or the curves of the parametric relationships.

* * * * *